United States Patent
Rabe et al.

(10) Patent No.: US 11,513,092 B2
(45) Date of Patent: Nov. 29, 2022

(54) TEMPERATURE-REGULATED GAS SENSOR WITH GAS SELECTIVE FILTER

(71) Applicant: Sensirion AG, Stäfa (CH)

(72) Inventors: Michael Rabe, Stäfa (CH); Robert Meyer-Piening, Stäfa (CH); Matthias Studer, Stäfa (CH)

(73) Assignee: Sensirion AG, Stäfa (CH)

( * ) Notice: Subject to any disclaimer, the term of this patent is extended or adjusted under 35 U.S.C. 154(b) by 210 days.

(21) Appl. No.: 17/029,133

(22) Filed: Sep. 23, 2020

(65) Prior Publication Data
US 2021/0088464 A1 Mar. 25, 2021

(30) Foreign Application Priority Data

Sep. 24, 2019 (EP) ..................................... 19199269

(51) Int. Cl.
*G01N 27/12* (2006.01)
*G01N 33/00* (2006.01)

(52) U.S. Cl.
CPC ......... *G01N 27/123* (2013.01); *G01N 27/125* (2013.01); *G01N 33/0014* (2013.01); *G01N 33/0016* (2013.01); *G01N 27/128* (2013.01)

(58) Field of Classification Search
CPC ............... G01N 27/125; G01N 27/123; G01N 33/0014; G01N 33/0016; G01N 27/128
See application file for complete search history.

(56) References Cited

FOREIGN PATENT DOCUMENTS

| WO | 2014012951 A1 | 1/2014 |
|---|---|---|
| WO | 2018053656 A1 | 3/2018 |

*Primary Examiner* — Benjamin R Schmitt
(74) *Attorney, Agent, or Firm* — Renner, Otto, Boisselle & Sklar, LLP

(57) ABSTRACT

The invention is directed to a gas sensor that includes a hotplate, a support structure, a gas selective filter, and circuitry. The support structure is configured to define a cavity. The gas selective filter is held by the support structure and spans the cavity. Various components are connected to the circuitry, and may include a temperature sensor element, a gas sensing element, and a heater. The temperature sensor element is configured to sense a temperature $T_f$ of the filter. The gas sensing element is sensitive to a target gas in the cavity. The heater is in thermal communication with the gas sensing element. The circuitry is configured to operate the sensing element, estimate a temperature $T_f$ of the filter, and regulate the heater. The circuitry regulates an extent to which power is supplied to the heater based on the estimated temperature $T_f$ of the filter.

20 Claims, 7 Drawing Sheets

TEMPERATURE-REGULATED GAS SENSOR WITH GAS SELECTIVE FILTER

BACKGROUND

The invention relates in general to the field of gas sensors and methods of operating such sensors. In particular, the invention relates to sensors relying on sensing materials such as metal oxides, which are heated to operate the sensor, and are equipped with filters such as fluoropolymer-based filters.

Gas sensors are known for detecting gases based on a variety of techniques. Such sensors include at least one sensing (or active) element sensitive to the presence or concentration of one or more gases. One known class of gas sensors are catalytic gas sensors, or pellistors, which detect the presence of combustible and oxidizing gases. Another class of gas sensor involves chemiresistors, i.e., materials for which the electrical resistance changes in response to changes in their direct chemical environment. In each case, the sensing material may contain a metal oxide material. Metal oxides may be used for the detection of analytes such as volatile organic compounds (VOCs), carbon monoxide, nitrogen dioxide, methane, ammonia or hydrogen sulphide and thiols.

Such sensor devices typically require a heater to heat the sensing material and can be integrated onto a semiconductor substrate. In metal oxide sensors, gaseous analytes interact with the heated metal oxide layer. As a result of the interaction, the conductivity of the sensitive film may change, and the change may be measured.

However, the sensing element, at which the target gas is converted into electrical signals, may adversely be affected by other gases present in the medium being measured, hence the need of a filter.

For example, WO2014012951 (A1) describes a gas sensor comprising an active element and a filtering cap, wherein the cap comprises a porous filtering element for counteracting the ingress of one or more atmospheric gases to the active element.

WO2018053656 (A1) describes a gas sensor comprising a support structure forming a cavity, wherein a sensing element sensitive to a gas is arranged in the cavity, and a size selective filter spanning the cavity. The size selectivity of the filter is determined by the size of pores in the filter material. The filter material preferably comprises or consist of a fluoropolymer, e.g., an amorphous fluoropolymer.

In both cases, there is a separation between the sensing element and the filter. The separation, or gap, between the filter and the active (sensing) element has been found advantageous to avoid thermal losses from the active element. Thermal losses may be of concern in the design of small-scale active elements, for example based on MEMS technology. In addition, the separation between the filter and the sensing element makes it possible for the sensing element to be operated at elevated temperatures, e.g., higher than 350 C or even 400 C, without damaging the filtering cap.

SUMMARY

According to a first aspect, the present invention is embodied as a gas sensor. The gas sensor basically comprises a hotplate, a support structure, a gas selective filter, and a circuitry. The support structure is configured so as to define (or contribute to define) a cavity. It further supports the hotplate. The gas selective filter is held by the support structure. This filter spans the cavity. The filter may notably be designed to filter gas molecules according to their sizes. The circuitry includes one or more integrated circuits. Beside the integrated circuits, various components are connected to the circuitry. Such components include a temperature sensor element, a gas sensing element, and a heater. The temperature sensor element is arranged on or in a part of the support structure. The temperature sensor element is configured to sense a temperature $T_f$ of the filter. The gas sensing element is arranged on or in the hotplate, so as to be sensitive to a target gas in the cavity. The heater is arranged on or in the hotplate, so as to be in thermal communication with the gas sensing element. The circuitry, as a whole, is configured to operate the sensing element, estimate a temperature $T_f$ of the filter, and regulate the heater. The circuitry operates the gas sensing element by: (i) supplying power to the heater for the latter to heat the gas sensing element; and (ii) processing signals received from the gas sensing element. The circuitry estimates the temperature $T_f$ of the filter based on signals received from the temperature sensor element. Finally, the circuitry regulates an extent to which power is supplied to the heater based on the estimated temperature $T_f$ of the filter.

The filter prevents a degradation of the gas sensor (and specifically its sensing element) by an exposure to detrimental gases. Now, the filter may be subject to a behavioural change in practice, as the present inventors observed. That is, the permeability of the filter to detrimental gas molecules may abruptly increase above a certain threshold temperature. Such a phenomenon can for example be observed when the filter is subject to unintentional heat from sources other than the heater, which is meant to heat the sensing material, not the filter. Thus, regulating the temperature of the heater by taking into account the estimated temperature of the filter allows the sensing material to be brought back to a safe temperature, if necessary. A "safe temperature" is a temperature at which detrimental molecules (as allowed by the filter owing to said behavioural change) do not damage the sensing material anymore. To achieve this, the circuitry is configured to regulate the heater based on a temperature of the filter that is estimated by the circuitry.

In practice, the circuitry may notably be configured to lower the extent to which power is supplied to the heater or to switch it off if the estimated temperature $T_f$ of the filter exceeds a threshold temperature. Conversely, the circuitry may possibly be configured to raise the extent to which power is supplied to the heater or to switch it on if the estimated temperature $T_f$ of the filter falls short of a threshold temperature, where the latter may possibly differ from the previous threshold temperature.

A cyclical operation of the sensing element will likely take place. That is, after having lowered or switched off the heater because the filter temperature has exceeded a threshold temperature (e.g., a first threshold temperature), the circuitry may cause to raise the extent to which the heater is powered or switch it on if the estimated temperature $T_f$ of the filter falls short of a threshold temperature (e.g., a second threshold temperature, lower than the first threshold temperature). Later on, the circuitry may, if necessary, lower/switch off the heater again, and so on. Thus, in embodiments, the circuitry is further configured to operate the gas sensing element by intermittently supplying power to the heater. I.e., the circuitry switches off the heater if the estimated temperature $T_f$ of the filter exceeds a threshold temperature or switch on the heater if the estimated temperature falls short of a threshold temperature.

Preferably, said temperature sensor element is a first temperature sensor element and the gas sensor further includes a second temperature sensor element that is connected to the circuitry. In that case, the circuitry may further be configured to: (i) estimate a temperature $T_s$ of the gas sensing element based on signals received from the second temperature sensor element; and (ii) regulate the extent to which power is supplied to the heater based on the estimated temperature $T_s$ of the gas sensing element, in addition to the estimated temperature $T_f$ of the filter.

The gas sensing element may possibly comprise a metal oxide material, in which case the circuitry is configured to operate the gas sensing element by supplying power to the heater for the latter to reach a temperature that is between 100 C and 600 C. The metal oxide material will thus reach a similar temperature, in operation. The circuitry may optionally be configured to operate the sensing element according to a temperature-controlled process, in which case a temperature of the sensing element need be measured (or estimated) by the circuitry. An intermittent operation of the sensing element is particularly advantageous when the sensing element comprises a metal oxide material.

Preferably, the gas sensor further includes a humidity sensor element connected to the circuitry. The circuitry may accordingly be configured to estimate an absolute humidity from signals received from the humidity sensor element and regulate the extent to which power is supplied to the heater based on each of: (i) the estimated absolute humidity, (ii) the estimated temperature $T_f$ of the filter, and (iii) the estimated temperature $T_s$ of the gas sensing element. This can be helpful as humidity too may cause to damage the sensing element.

In embodiments, the filter comprises a fluoropolymer. That is, the filter comprises a material that includes or consists of a fluoropolymer, preferably an amorphous fluoropolymer whose free fraction per volume is at least of 19%, and more preferably between 20% and 40%. Despite appealing filtering properties, such materials may exhibit a behavioural change such as discussed above. Namely, above a certain threshold temperature, they become substantially more permeable to certain gas molecules (e.g., siloxane) that may endanger the metal oxide sensing material. For this reason, the circuitry may, in embodiments, be configured to lower the extent to which power is supplied to the heater or to switch it off if the estimated temperature $T_f$ of the filter exceeds a threshold temperature that is between 47 C and 130 C, preferably between 62 C and 89 C, e.g., between 62 C and 68 C.

In preferred embodiments, the support structure further comprises a semiconductor chip. One or more of the integrated circuits may for instance be integrated in said semiconductor chip. The support structure may optionally include an encapsulation defining one or more surfaces of the cavity, wherein the semiconductor chip is partly embedded in the encapsulation.

In embodiments, the temperature sensor element and all of said one or more integrated circuits are integrated in said chip. In addition, the temperature sensor element is preferably arranged in a body of the chip, hence yielding a very compact chip package.

In variants, said semiconductor chip is a first semiconductor chip and the gas sensor further comprises a second semiconductor chip, which includes at least one of the one or more integrated circuits. All of said integrated circuits may be included in the second chip, as in embodiments. In addition, the temperature sensor element may be arranged on or in the second semiconductor chip, for example in a body of the second semiconductor chip. Integrated circuits that are included in the second chip may possibly be connected to one or more integrated circuits included in the first chip, so as for the gas sensing element to be jointly operated by integrated circuits of both the first chip and the second chip, in operation. Such embodiments make it possible to take advantage of a temperature sensor element chip, which can be joined and connected to the sensing chip in a same package, for example.

In other variants, the support structure comprises a container with an aperture spanned by the filter, a printed circuit board, and a connector wired to the printed circuit board. The gas sensor may notably comprise one or more semiconductor chips arranged on the printed circuit board, wherein said chips include the gas sensing element, the temperature sensor element, and the integrated circuits.

In preferred embodiments, the support structure further includes a substrate (e.g., a semiconductor substrate), which is structured so as to form a membrane. The substrate may for example comprise an opening (or recess) extending at least partly through the substrate, while the membrane extends over said opening. This opening may possibly be distinct from the cavity. E.g. the opening may be provided on one side of the substrate, while the cavity may be formed on the other side of the substrate. The temperature sensor element may for instance be arranged on or in said substrate.

In general, the hotplate can notably be configured as a membrane, a slotted membrane, or a bridge. Yet, any hotplate configuration can be contemplated. When the hotplate is configured as a membrane, the heater may advantageously form part of (i.e., be integrated in) the membrane, so as to be resistively heated, in operation of the gas sensor. The membrane may actually be embodied as a resistively-heated element, in which case the heater and the membrane are one and a same thing.

According to another aspect, the invention is embodied as a method of sensing a target gas with a gas sensor. The method involves a gas sensor such as described above. I.e., the sensor comprises a hotplate, a support structure (defining a cavity and supporting the hotplate), a gas selective filter maintained by the support structure and spanning the cavity, and a circuitry including one or more integrated circuits, as well as a set of components that are, each, connected to the circuitry. Said components include a temperature sensor element, a gas sensing element, and a heater, as described above. The method is performed via the circuitry. The method comprises operating the gas sensing element by: (i) supplying power to the heater for the latter to heat the gas sensing element; and (ii) processing signals received from the gas sensing element. In addition, a temperature $T_f$ of the filter is estimated based on (i.e., by taking into account) signals received from the temperature sensor element. Moreover, the extent to which power is supplied to the heater is regulated based on the estimated temperature $T_f$ of the filter.

For example, the extent to which power is supplied to the heater may be lowered or the heater be switched off if the estimated temperature exceeds a threshold temperature, as in embodiments. Conversely, the extent to which power is supplied to the heater may possibly be subsequently raised or the heater be switched on if the estimated temperature falls short of a threshold temperature (again, the latter is not necessarily the same as the previous threshold).

In embodiments, the set of components of the gas sensor provided comprises several hotplates (including the above hotplate), wherein each of the hotplates is supported by the support structure. In addition, several gas sensing elements (including said sensing element) are arranged on or in a respective one of the hotplates. The gas sensing elements are sensitive to distinct target gases. Moreover, several heaters (including said heater) are involved, which are arranged on or in a respective one of the hotplates, so as to be in thermal communication with respective ones of the gas sensing elements. Finally, one or more temperature sensor elements are provided (including said temperature sensor element), which are arranged on or in a part of the support structure. In that case, the method comprises (again, via the circuitry) operating the gas sensing elements by: (i) supplying power to their respective heaters for the latter to heat the respective gas sensing elements at distinct working temperatures; and (ii) processing signals received from the gas sensing elements. The temperature $T_f$ of the filter is estimated based on signals received from the one or more temperature sensor elements. Moreover, the method further comprises individually regulating extents to which power is supplied to the heaters based, on the one hand, on the estimated temperature $T_f$ of the filter, and, on the other hand, on distinct threshold temperatures associated to the sensing elements.

Devices and methods embodying the present invention will now be described, by way of non-limiting examples, and in reference to the accompanying drawings.

BRIEF DESCRIPTION OF SEVERAL VIEWS OF THE DRAWINGS

The accompanying figures, where like reference numerals refer to identical or functionally similar elements throughout the separate views, and which together with the detailed description below are incorporated in and form part of the present specification, serve to further illustrate various embodiments and to explain various principles and advantages all in accordance with the present disclosure, in which:

FIG. 8 is a 2D cross-sectional view of a support structure having a membrane configuration, showing a patch of sensing material arranged on the support structure, as involved in embodiments;

Figure 1:
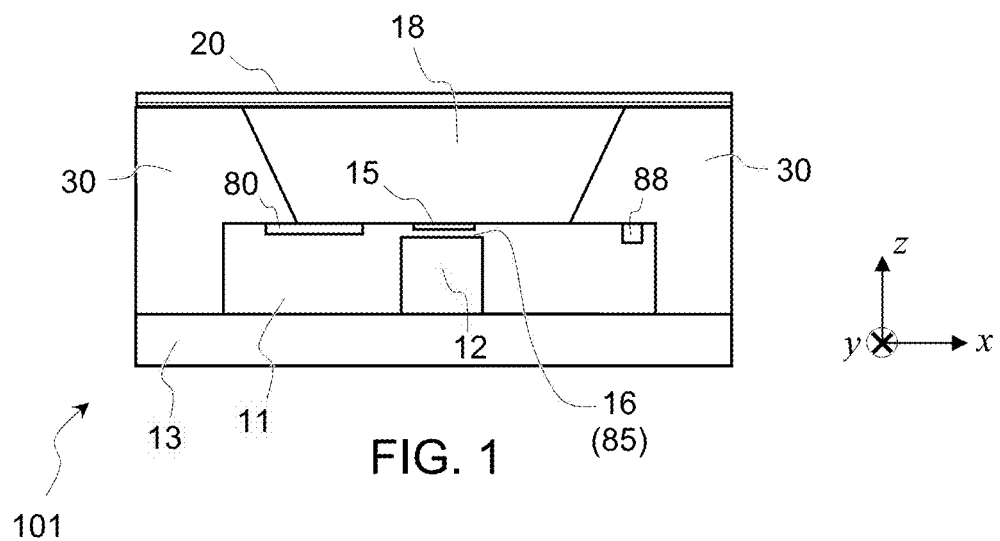
FIGS. 1-8 are 2D cross-sectional views of gas sensors according to various embodiments. Such sensors may involve a single semiconductor chip or substrate (as in FIGS. 1, and 5-7). In variants, the gas sensors include several semiconductor chips, as in FIGS. 2-4. The chips may possibly be encapsulated, at least partly (as in FIGS. 1-5, and 7), or arranged on a printed circuit board (as in FIGS. 3 and 4), where the printed circuit board may possibly be arranged in a container, in which an aperture is defined and shut by a filter (FIG. 4)

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION OF EMBODIMENTS OF THE INVENTION

As discussed in the background section, prior gas sensors are sometimes equipped with sensing elements that include materials that are heated to operate the sensor, using a hotplate. Such sensors may further include a filter to protect the sensing material, where the filter is preferably distant from the hotplate, so as not to be damaged by the latter. Now, as the present inventors observed, this filter may nevertheless happen to be (e.g., unintentionally) subject to heat in practice, even though the operation of the device does not require heating the filter. There, a problem that raises is that the heated filter may exhibit a behavioural change due to temperature. Namely, the filter may suddenly become more permeable to certain gas molecules (call them "detrimental molecules") that may damage the sensing material of the sensor, all the more as the sensing material is heated. And as the present inventors further realized, this behavioural change occurs above a certain threshold temperature of the filter. This threshold temperature depends on the exact composition of the filter material. The reason for this phenomenon is currently not well understood. Thus, even where the filter of the gas sensor is not meant to be heated to operate the gas sensor, the practical conditions in which the sensor is operated may cause to lower the performance of the filter and/or damage the sensing material.

The present Inventors have accordingly devised a conceptually simple solution to this problem, which takes into account the temperature of the filter, in order to regulate the temperature of the heater when operating the gas sensing element. By regulating the temperature of the heater according to the temperature of the filter (and possibly other parameters too), the sensing material may, if necessary, be brought back to a safe temperature, at which detrimental molecules do not damage the gas sensing material anymore. To that aim, the circuitry must be configured to suitably regulate the heater by taking into account the temperature of the filter. There, another practical issue is that usual temperature sensor elements as provided in gas sensors are normally used for the temperature-controlled operation of the sensing material, and not for measuring the temperature of the filter. In the present context, the temperature of the filter must be estimated based on outputs from a temperature sensor element that is suitably positioned in the gas sensor to allow the filter temperature to be measured. This additional task is advantageously performed by an aptly configured circuitry, including, e.g., a signal processor, one or more controllers, etc. In fact, it is possible to leverage processing units and controllers as already provided in performant sensors and configure such units for them to additionally estimate the filter temperature, e.g., in addition to estimating the temperature of the heater and/or the sensing material, if needed.

A first aspect of the invention is now described in detail in reference to FIGS. 1-9 and 13, which concerns a gas sensor 101-110.

The gas sensor notably comprises a support structure 11, 30, 50, 70 and a hotplate 16, 16a. The support structure 11, 30, 50, 70 is designed so as to support the hotplate. However, the hotplate remains functionally distinct from the support structure in terms of thermodynamics and mechanics, as discussed later in detail. The support structure further defines (or contributes to define) a cavity 18. I.e., the support structure defines one or more surfaces enclosing this cavity. The support structure typically comprises multiple parts or components, e.g., a substrate or a chip 11, or several substrates or chips, an encapsulation 30, a printed circuit board (PCB) 50, a container 70, etc., as in embodiments discussed herein. One or several of said parts or components may define (or contribute to define) the cavity 18.

The gas sensor further comprises a gas selective filter 20, which is held by the support structure. That is, the filter 20 is maintained by, i.e., held by or otherwise attached to the support structure. The gas selective filter 20 is arranged so as to span the cavity 18. The filter typically spans a substantial aperture provided in the support structure, above the cavity. The filter is thus distant from the hotplate and not in direct contact with sensing material.

The filter may notably be designed to filter gas molecules according to their sizes. This filter may for example be embodied as a molecular sieve or as a fluoropolymer-based filter, as described below in detail. In variants, an adsorption filter may be relied on. Ideally, the filter is permeable to gas molecules to be detected (the "target gas") by the sensing element and non-permeable for one or more other gases. Such other gases may notably include detrimental gas molecules (e.g., siloxane molecules and variants thereof) that are prone to react with the material of the sensing element and degrade its sensing capabilities over time.

Moreover, the gas sensor comprises a circuitry 80, which includes one or more integrated circuits (ICs), i.e., one or more sets of circuits that are integrated in components of the sensor, such as one or more PCBs, semiconductor chips, etc. The ICs of the circuitry 80 may possibly be interconnected. In this document, an IC refers to a set of electronic circuits (e.g., integrated in a semiconductor chip or a component thereof), whereas a semiconductor chip may include one or more ICs. While an IC is often referred to as a chip or microchip in the literature, a semiconductor chip is, in the present document, primarily referring to a physical object that comprises the IC(s), whereas an IC primarily refers to the electric circuit and electronic components making up this IC. Thus, one understands that the present circuitry 80 may include electric circuits with electronic components (such as electronic components 81-84, 86, and 89 in the example of FIG. 9), wherein said electronic components may possibly be distributed across several parts (such as semiconductor chips or substrates) of the gas sensor or integrated in or on one of said parts.

Beside IC components, additional components of the gas sensor are connected to the circuitry. These additional components include a temperature sensor element 88, a gas sensing element 15, and a heater 85, as described below.

The temperature sensor element 88 is configured to sense a temperature $T_f$ of the filter 20. The temperature sensor element 88 is arranged on or in a part of the support structure 11, 30, 50, 70. The temperature sensor element 88 may for example include a thermal sensing element 88, i.e., a probe connected to a temperature sensor element circuit 87, as assumed in FIG. 9. The sensing element 88 is arranged in or on a part of the support structure that is distinct from the hotplate. For example, it may be located on or in the body of a chip 11 or a substrate supporting the hotplate (as in FIG. 1), or on/in a different chip 40 (as in FIG. 2). In all cases, the sensing element 88 is arranged so as not to be impacted by the hotplate.

The gas sensing element 15 is arranged on or in the hotplate 16, 16a, so as to sense a given target gas (or possibly distinct target gases) in the cavity 18. The gas sensing element 15 is for example arranged on the top surface of (or partly embedded in) a superficial thickness of the hotplate, where the latter is, e.g., formed as a membrane. The hotplate will typically be exposed in the cavity 18, unless it is entirely concealed by the gas sensing element 15. Several variants can be contemplated, as the person skilled in the art will appreciate.

The heater 85 is arranged on or in the hotplate 16, 16a, so as to heat the latter and, in turn, the gas sensing element 15. The heater 85 is likely arranged in proximity with a sensing material 152 of the sensing element 15 (see, e.g., FIG. 8) and is therefore in thermal communication therewith. The heater 85 may also be embodied as a resistively-heated hotplate, in which case the hotplate and the heater are one and a same thing. Since the gas sensing element 15 is arranged on or in the hotplate 16, 16a, whereas the filter 20 spans the cavity 18 and is thus distant from the hotplate, the heater 85 is in (much) closer thermal communication with the gas sensing element 15 (e.g., in thermal contact therewith) than with the filter 20.

As a result, the heater will normally not heat (or at least not substantially heat) the filter 20, in operation. However, the filter may, in practice, be subject to unintended heat due to external factors, such as sunlight or other radiations, e.g., heat radiated from other components of the device. Thus, heat arising from external factors may happen to impact the filter temperature much more than heat from the heater 85 in practice. And this may result in damaging the sensing element 15, for reasons explained later.

To address this issue, the circuitry 80 is here configured to perform three tasks, which include the operation of the sensing element 15, the estimation of the temperature $T_f$ of the filter 20, and the regulation of the heater 85.

Figure 9:
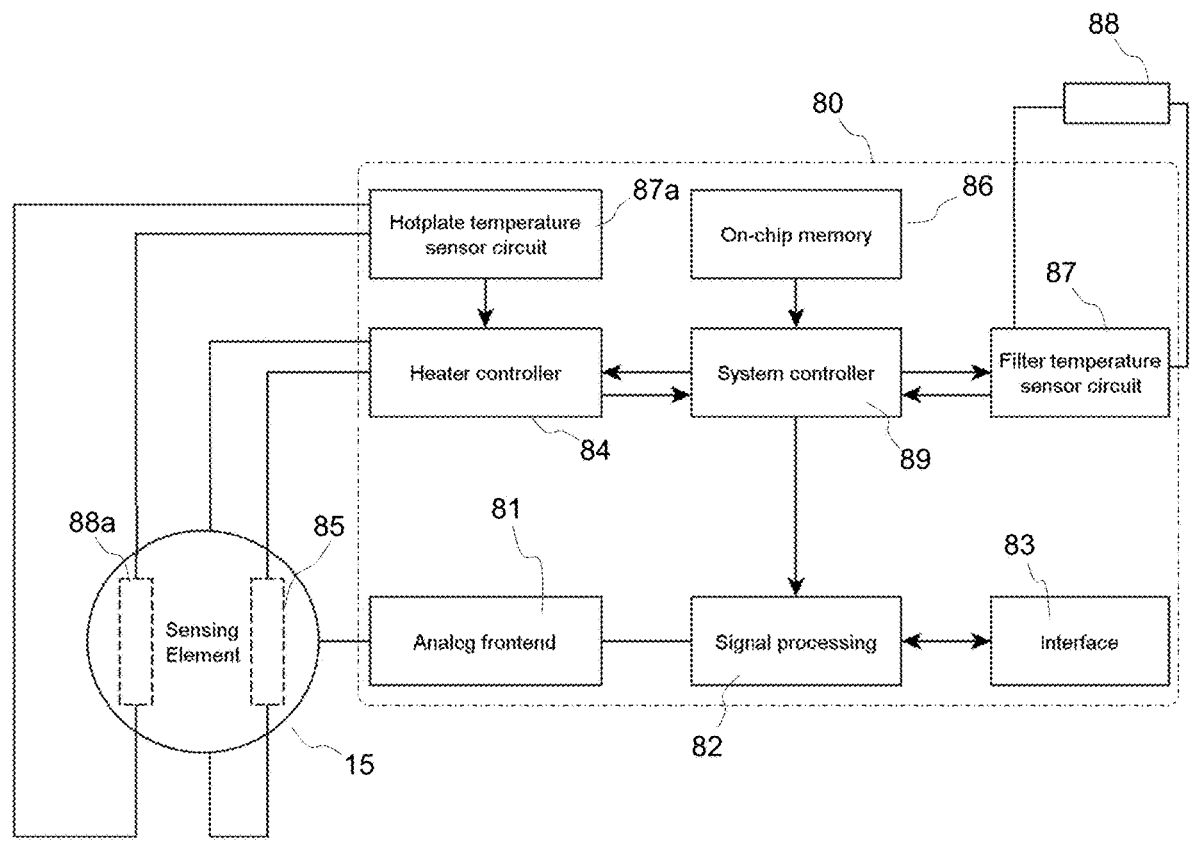
FIG. 9 is a block diagram schematically illustrating selected components of a circuitry of a gas sensor according to embodiments.

In detail, the circuitry operates the gas sensing element 15 by supplying power to the heater 85. E.g., the circuitry energizes the heater 85 via a heater controller 84, itself driven by a system controller 89, as illustrated in FIG. 9. This causes the heater 85 to heat the gas sensing element 15, in operation. Note, the cavity ensures a separation or gap between the filter 20 and the sensing element, thanks to which the sensing element 15 can be operated at elevated temperatures, e.g., higher than 350 C or even 400 C, without damaging the filter 20. In addition, signals received from the sensing element 15 can be processed by the circuitry (e.g., via a signal processor 82, see FIG. 9), to read a signal representative of target gas molecules that are sensed by the gas sensing element 15. Thus, the gas sensor may possibly compute a target gas concentration or forward signals processed by the signal processor 82 to another processing unit, for it to compute and provide any useful feedback in respect of the sensed gas (e.g., a gas concentration) to a user, for example.

The temperature $T_f$ of the filter 20 is estimated based on signals received from the temperature sensor element 88, see FIG. 9. Note, "estimate the temperature $T_f$ of the filter" means determine or measure this temperature or an approximation thereof, which may possibly be a very close approximation of the true temperature of the filter, owing to sensor configurations as described herein.

Figure 12:
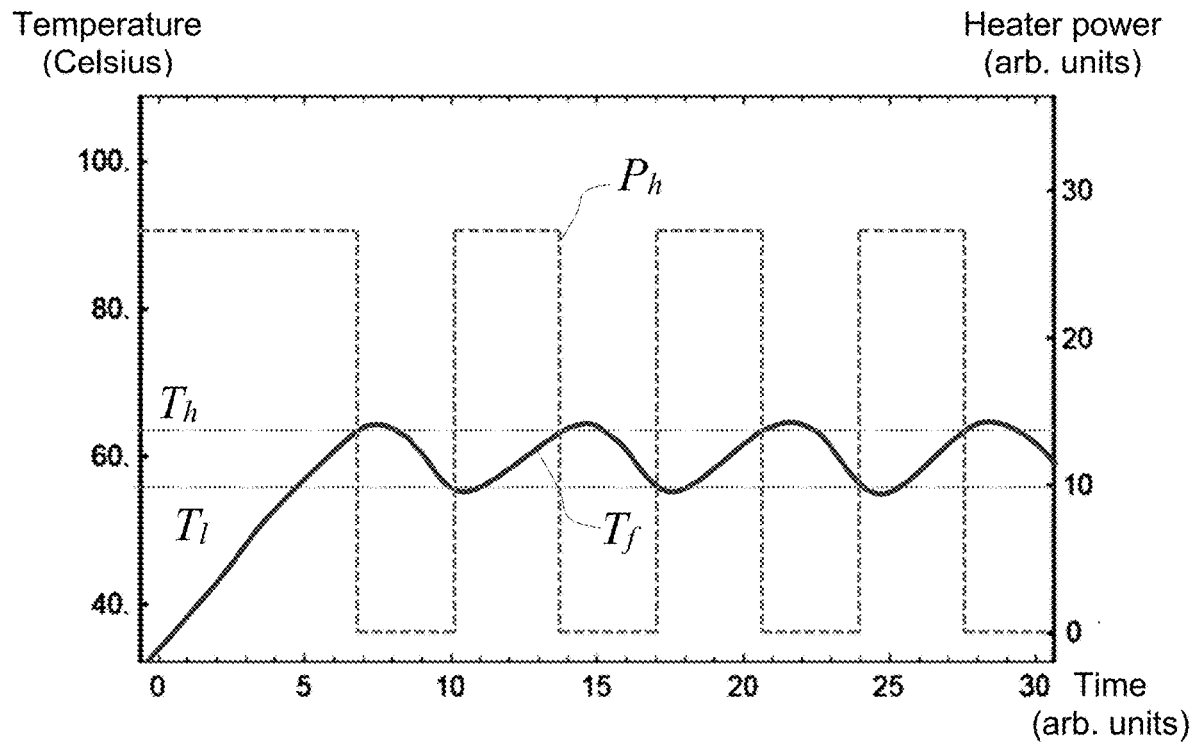
FIG. 12 is a graph representing a temporal evolution of the temperature of the filter of a gas sensor according to embodiments, together with the concomitant operation of the heater of the sensing material of the gas sensor, as involved in embodiments.

Finally, the circuitry regulates the extent to which power is supplied to the heater 85 based on the estimated temperature $T_f$ of the filter 20. In practice, regulating the temperature of the heater means lowering or raising the extent to which the heater is energized (via an electrical signal, i.e., a voltage or more likely a current signal), or switching off and on the heater. This translates into a varying electrical power $P_h$ being dissipated in the heater, as illustrated in FIG. 12.

The present approach makes it possible to prevent a degradation of the gas sensor, and specifically its sensing element 15, resulting from an exposure to detrimental gases. For example, siloxane, or more generally volatile silicon-containing compounds, may damage sensing elements, in particular metal oxide sensing elements. Such damages may notably increase the response time of the sensing element and also reduce the sensor signal. Thanks to the present gas sensor designs, an exposure to such detrimental gases is first prevented or at least mitigated by the filter 20. The filter is at a distance from the sensing element, so as not to be heated by the hotplate. The filter may notably act as a physical separator for gas molecules of different sizes. In particular, a fluoropolymer filter allows pores of desired sizes to be achieved, letting smaller target gas molecules pass while blocking larger, detrimental molecules. For example, a fluorinated filter protects the sensing element against aggressive chemicals such as acids or bases, and further prevents, by design, build-up of solids and liquids on the surface of the sensing element 15.

Moreover, by regulating the temperature of the heater according to the temperature of the filter, the sensing material can be brought back to a safe temperature, at which detrimental molecules allowed by the unintentionally heated filter 20 will not damage the sensing material anymore, in particular where this material includes or consists of a metal oxide. To achieve this, the circuitry is configured to regulate the heater by taking into account the temperature of the filter as estimated by the circuitry.

Comments are in order. As evoked above, the hotplate 16, 16a is functionally distinct from the support structure, even though it is supported by the latter. Thus, the temperature sensor element 88, which is arranged on/in a part of the support structure, is assumed to be sufficiently distant from the hotplate, and located so as be able to sense a temperature $T_f$ of the filter 20.

In more detail, the hotplate 16, 16a may possibly be configured as a membrane, a slotted membrane, or a bridge, as known per se. The hotplate may notably be provided on or as part of a substrate, or a chip, for example. Now, such a substrate or chip may be regarded as forming part of the support structure. Incidentally, this substrate or chip may contribute to define the cavity 18, just like other parts 30, 70 of the support structure, as in embodiments discussed herein. However, the hotplate remains functionally distinct (thermally or mechanically speaking) from the chip or substrate, owing to the respective functions of the support structure (which supports or holds elements) and the hotplates (meant to heat the gas sensing element 15).

Accordingly, while the body of a chip or a substrate of the gas sensor can be considered to form part of the support structure, as in embodiments, the hotplate (e.g., a membrane) is not considered to form part of the support structure in this document. This is consistent with the fact that, for example, the thermal conductivity from a membrane to the rest (i.e., the main body) of the chip or substrate is very limited or insignificant (if at all measurable) due to the very thin connections between the membrane and the body of the substrate. Plus, such a membrane normally has a very small thermal mass compared to the body of the chip or substrate due to its size (e.g., its thinness). For completeness, the cavity 18 will likely be essentially defined by the support structure (e.g., by lateral, inner surfaces of an encapsulation 30 and the upper peripheral surface of the main body of the substrate or the chip) and not by the hotplate 16, 16a. The latter is typically coated by a patch of sensing material and is thus not even exposed in the cavity anyway (it does accordingly not delimit the cavity). In other words, the function of the support structure is to support or hold elements of the gas sensor and to define a cavity therein, while the function of the hotplate is to heat the sensing element. For all the reasons above, the hotplate is considered to be distinct from the support structure in this document.

Figure 10:
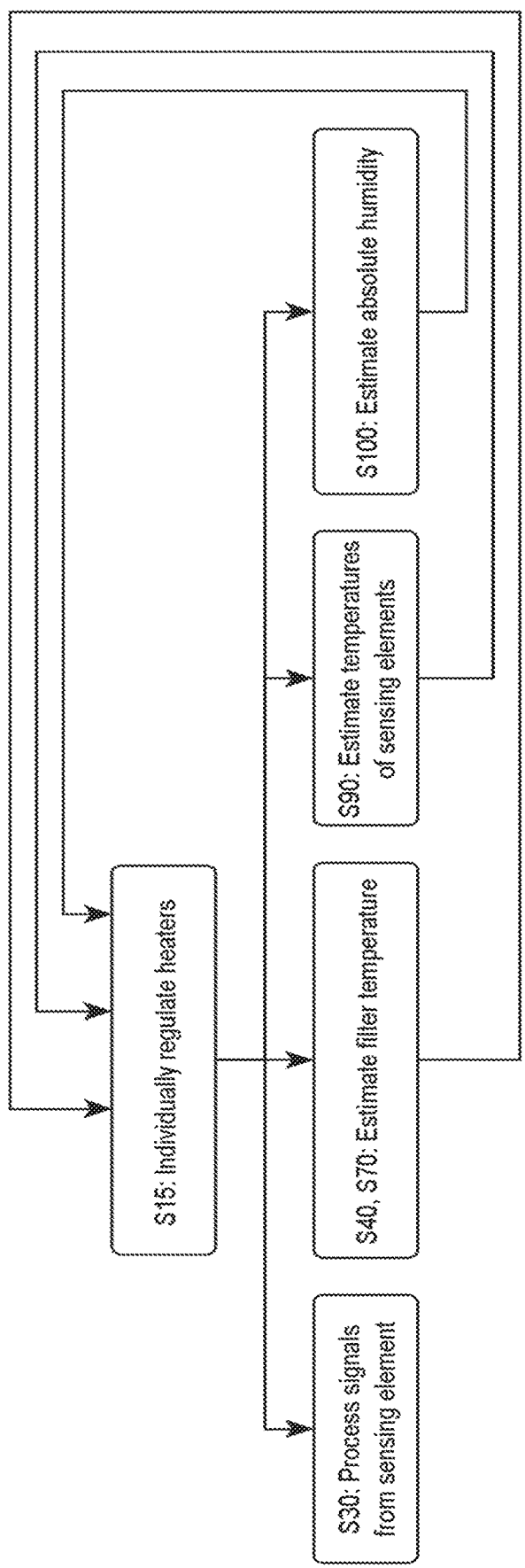
FIG. 10 is high-level flowchart illustrating main steps of a method of operating a gas sensor with multiple sensing elements, wherein the sensing elements are operated according to decoupled temperature-controlled processes, as in embodiments.
Figure 11:
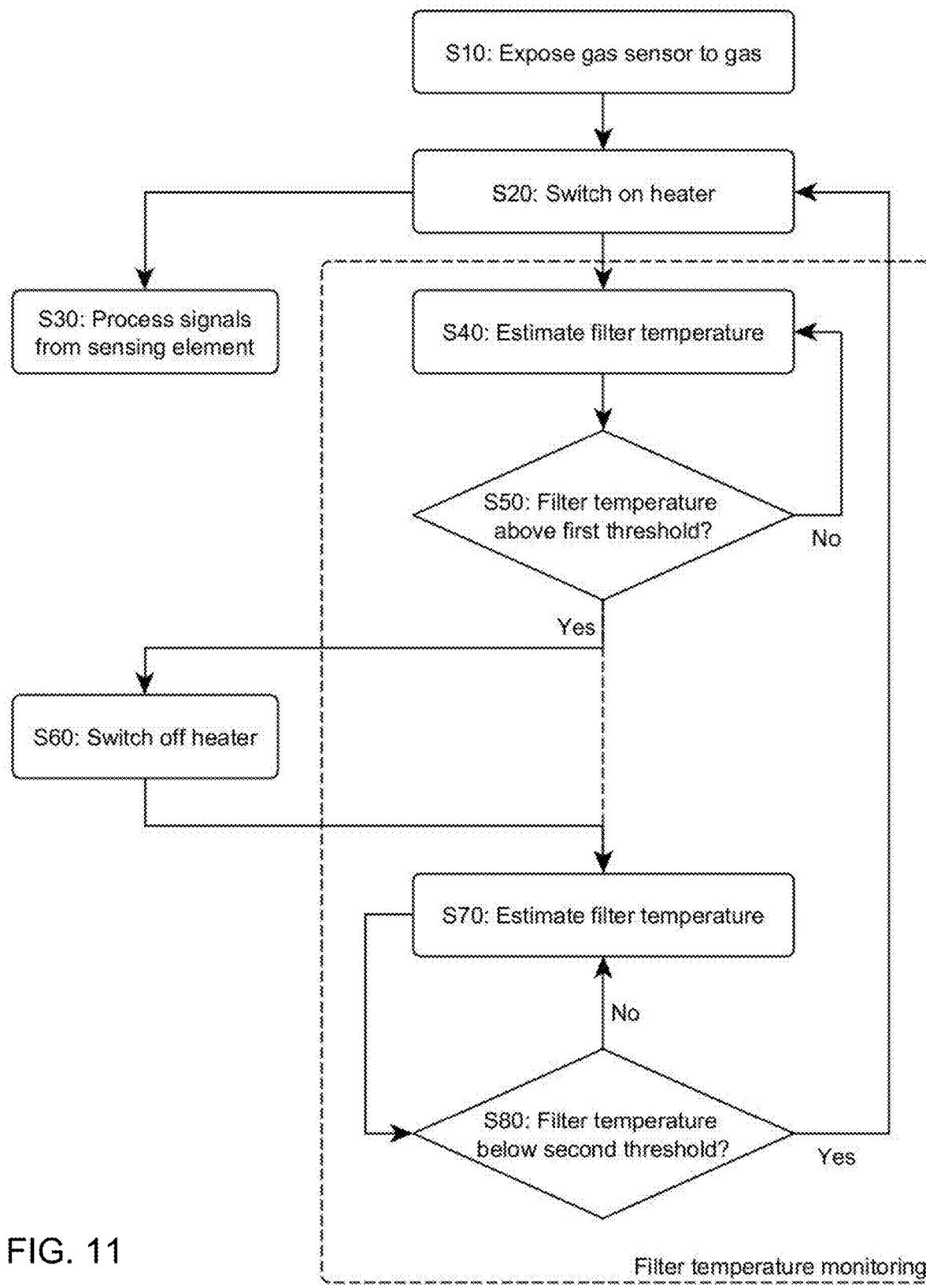
FIG. 11 is another flowchart illustrating steps of a method of intermittently operating a gas sensor, based on an estimated temperature of the filter, according to embodiments.

Various aspects of the present gas sensors are now described in detail, in reference to particular embodiments of the invention. To start with, and as illustrated in FIGS. 10-12, the circuitry 80 may notably be configured to lower the extent to which power is supplied to the heater 85 (or simply switch it off) if the estimated temperature $T_f$ of the filter 20 exceeds a threshold temperature, e.g., a first threshold temperature $T_h$. And conversely, the circuitry 80 may further be configured to raise the extent to which power is supplied to the heater 85 (or switch it on) if the estimated temperature $T_f$ of the filter 20 falls short of a threshold temperature, e.g., a second threshold temperature $T_l$. Different threshold temperatures may possibly be relied on, as assumed in the flowchart of FIG. 11 and the graph of FIG. 12, where the first threshold $T_h$ is higher (by a few degrees) than the second threshold $T_l$. In practice, the first threshold $T_h$ should preferably be (slightly) lower than a critical temperature of the filter 20, above which the filter becomes prohibitively permeable to detrimental gas molecules, to account for thermodynamics of the gas sensor, e.g., remanence effects.

In operation, once the circuitry switches off the heater, the gas sensor (or any processing unit connected thereto) may possibly provide a feedback to a user (e.g., show a warning), and/or keep on showing a last gas concentration value as obtained from the gas sensor. For example, a message may be displayed (e.g., "Overheat warning, gas sensor is temporarily disabled") or the gas sensor may simply keep on showing a last gas concentration value as obtained before switching off the heater. More sophisticated approaches can further be used to keep on estimating the gas concentration value once the heater has been switched off, e.g., based on a parametric model, such as an analytic function involving variables such as time, the last known filter temperatures and the last gas concentrations observed.

Referring more specifically to FIG. 11, the circuitry 80 may notably be configured to operate the gas sensing element 15 by intermittently supplying power to the heater 85. In that case, the circuitry switches off the heater 85 if the estimated temperature $T_f$ of the filter 20 exceeds a (first) threshold temperature or switch on the heater 85 if the estimated temperature falls short of a (second) threshold temperature, see also FIG. 12. That is, the sensing element is operated in intervals and a mere on-off operation is relied on, for simplicity.

However, in more sophisticated variants, the electrical power $P_h$ dissipated in the heater 85 may vary (upon regulating the heater) as a smooth function of the filter temperature, e.g., as a polynomial or rational function of the estimated temperature of the filter, where this function is parameterized by the threshold temperature(s). That is, instead of completely switching on or off the heater, the latter may be smoothly regulated, so as to optimize the temperature dynamics of the sensing material. Given a suitable model of the thermodynamics of the device, such an approach can be exploited to optimize the time during which the sensing element 15 is effectively operated for measuring a target gas.

As illustrated in FIG. 10, the circuitry 80 may advantageously operate the heater 85 according to a temperature-controlled process that further takes into account the temperature $T_s$ of the gas sensing element 15 (e.g., of the heater and/or the sensing material of the sensing element), in addition to the temperature of the filter 20. Thus, an additional temperature sensor element 88a (e.g., a thermal sensing element) is preferably provided on or in the hotplate, see FIG. 9. This way, power may be supplied to the heater 85 based on additional feedback received from this temperature sensor element 88a. In other words, the circuitry may regulate the extent to which power is supplied to the heater 85 based on the estimated temperature $T_s$ of the gas sensing element, in addition to the estimated temperature $T_f$ of the filter 20. Such a temperature-controlled operation of the heater may particularly be desired when the sensing element 15 comprises a metal oxide material, as further discussed later.

Preferred embodiments of the circuitry 80 are now described in detail. The ICs of the circuitry may for example be integrated in one or more components (e.g., ASIC, MEMS, and/or CMOS chips) of the gas sensor. As seen in the functional diagram of FIG. 9, the circuitry 80 may for example include an evaluation and control unit 82, 89, which includes a signal processor 82 coupled to a system controller 89. In the example of FIG. 9, the main (i.e., system) controller 89 is connected to a heater controller 84, itself connected to the heater 85. The sensing element 15 is further connected to the signal processor 82 via an analog frontend 81, for the processor 82 to process (e.g., interpret) signals received from the sensing element 15, in operation.

In addition, the circuitry 80 may possibly include an on-chip memory 86, accessed by the system controller 89, and an interface 83, through which digital signals representative of the target gas and high-level instructions (e.g., to operate the heater) can be communicated. For completeness, the sensing element 15 is in thermal contact with the heater 85 and a thermistor 88a. The thermistor 88a forms part of a temperature sensor circuit 87a, controlled by the unit 84, to allow a temperature-controlled process of operation of the sensing material of element 15. A distinct temperature sensor circuit 87, 88 is provided for measuring the temperature of the filer 20, as evoked earlier. The circuit 87, 88 is connected to the system controller to provide the required temperature feedback.

As apparent from FIG. 9, the heater 85 can be used to heat a sensing material of the sensing element 15. The thermistor 88a is used to control the temperature of the sensing material. Both resistances 85, 88a are in thermal communication (in thermal contact) with, e.g., a patch of sensing material (see FIG. 8), to operate the sensing material according to a temperature-controlled process, so as for this material to reach a desired working temperature.

More generally, several sensing elements 15 (e.g., with distinct metal oxide materials) may be involved, each connected to the circuitry 80, where the circuitry can for instance be distributed across several chips, if necessary.

The circuitry 80 shown in FIG. 9 is configured to perform (or instruct to perform) and/or control various operations such as depicted in the flowcharts of FIGS. 10 and 11. That is, the circuitry 80 is programmed, designed, adapted, or otherwise configured to perform such operations.

Preferred materials are now discussed in detail. As evoked above, the sensing element 15 may notably comprise a metal oxide material (MOX). The MOX material may for instance include one or more of tin oxide, zinc oxide, titanium oxide, tungsten oxide, indium oxide and gallium oxide. In that case, the circuitry 80 may be configured to operate the heater 85 so as for the latter to reach a temperature between 100 C and 600 C. More generally, several metal oxide sensing elements 15 may be involved. Attention is drawn to materials as described in WO2018053656 (A1), which can advantageously be used as sensing materials in the present context as well.

The gas filter 20 may for instance comprises a selective, gas-permeable filter material 23, i.e., a material designed to counteract ingress of one or more types of atmospheric gases to the sensing element (e.g., a MOX material as per preferred embodiments discussed above), while allowing other types of gas molecules to diffuse therethrough and reach the sensing element 15. Thus, the filter may be chosen to counteract ingress of detrimental species, e.g., inhibiting and/or poisoning species, to the sensing element. In addition, the filter 20 may generally be designed to lower the background and therefore improve SNRs eventually obtained.

The filter material 23 may for instance comprise a microporous material, such as a zeolite, or an active carbon. In variants, other porous materials can be used, such as silicon dioxide or mesoporous silica. Combinations of such materials can be contemplated, if necessary.

In preferred variants, though, the filter material 23 includes or consists of a fluoropolymer. A fluoropolymer is a fluorocarbon-based polymer that exhibits multiple carbon-fluorine bonds. It usually has a high resistance to solvents, acids, and bases, so that it can advantageously be used for the present purpose. The polymer 23 is preferably an amorphous fluoropolymer, whose free fraction per volume is of at least 19%. Preferably, the free fraction per volume of the polymer 23 is between 20% and 40%. For example, amorphous fluoroplastics, e.g., Hyflon AD 80 or Hyflon AD 60 can be used, or amorphous fluoroplastics Teflon AF, e.g., Teflon AF 1600 or Teflon AF 2400, or a TTD homopolymer, or a Cytop homopolymer. Attention is again drawn to materials, as well as combinations of materials (copolymers) as described in WO2018053656 (A1), which can advantageously be used as filter materials in the present context too. The free fraction per volume and implications of preferred values thereof are also described in WO2018053656 (A1).

Figure 5:
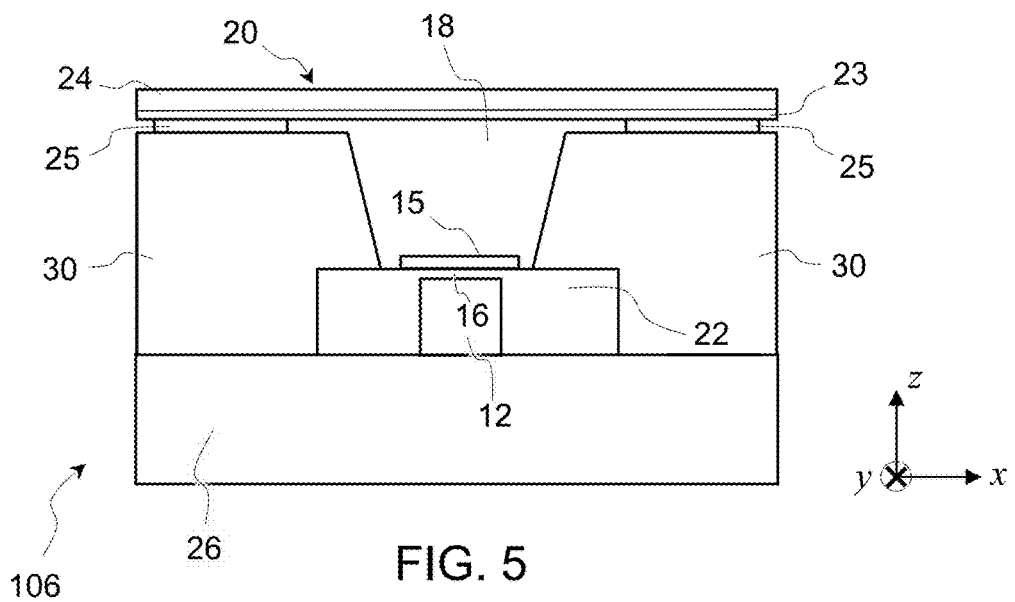
Figure 6:
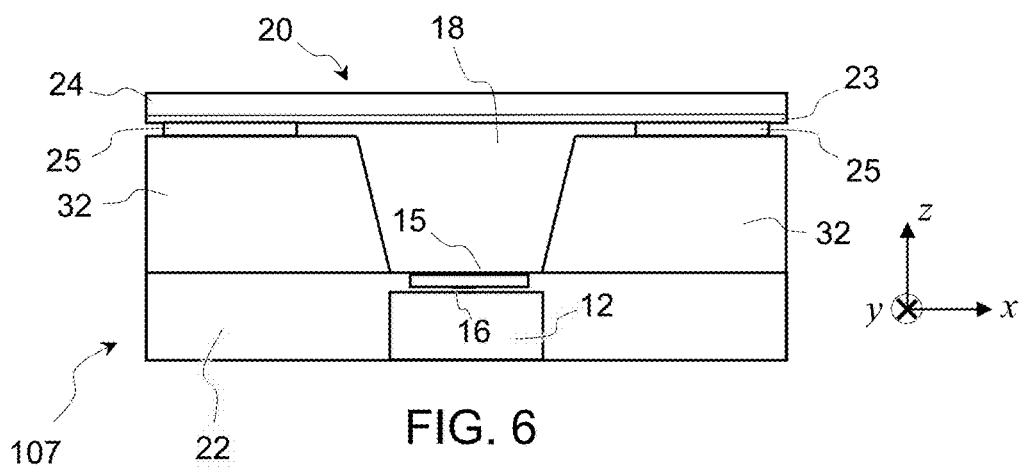
Figure 7:
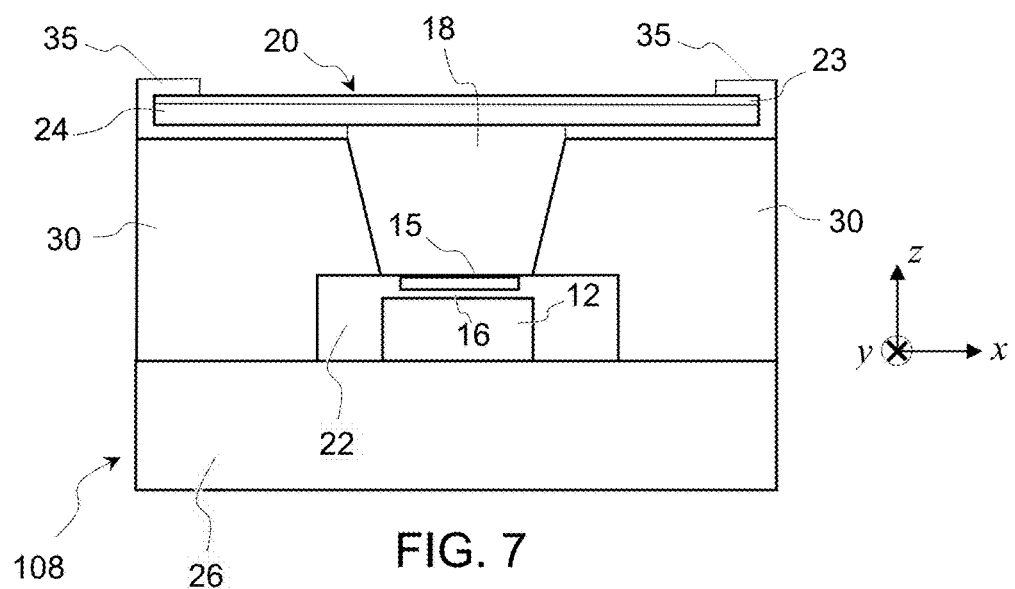

As best seen in FIGS. 5-7, the filter 20 preferably includes a thin layer 23, which may for instance comprise or consist of a fluoropolymer, as noted above. The layer 23 is preferably attached to a carrier 24, which provides mechanical stability to the filter and may also prevent the filter layer 23 to be subject to cracks. Note, the carrier material 24 too may possibly comprise or consist of a fluoropolymer layer. This is advantageous in that two layers of fluoropolymer, i.e., the filter layer 23 and the carrier layer 24, can easily attach to each other. Plus, such layers 23, 24 will more consistently react to temperature changes. The layers 23, 24 can be prepared in such a way that the average size of pores of the carrier material 24 exceeds the average size of pores in the filter layer 23. I.e., the carrier is more permeable to gas molecules than the filter layer 23, so as not to impair the function of the filter layer 23.

Now, despites the merits of fluropolymer-based filters, such materials may only be effective under a certain threshold temperature, which typically is between 47 C and 130 C (or possibly between 62 C and 89 C or, even, between 62 C and 68 C), as the present Inventors observed. The exact threshold temperature depends on the exact composition and structure of the material 23. As said, the reasons for this phenomenon is still unclear. Still, the circuitry 80 may advantageously be designed to lower the extent to which power is supplied to the heater 85 or even to switch it off if the estimated temperature $T_f$ of the filter 20 exceeds a threshold temperature $T_h$ falling in ranges as given above, namely between 47 C and 130 C, or between 62 C and 89 C or, even, between 62 C and 68 C, as assumed in FIG. 12. For example, the temperature $T_h$ may be of approximately 65 C. Note, the precision of the above temperature values is given by the last digit, i.e., ±1 C.

The temperature value $T_h$ considered is preferably taken to be slightly smaller than the actual, critical temperature of the material 23, above which the effectiveness of the material abruptly changes. In addition, the temperature $T_l$ at which the heater may be reactivated is preferably distinct from and smaller than $T_h$, as illustrated in FIG. 12. A gap between the threshold temperatures $T_h$ and $T_l$ is useful to prevent too frequent or untimely commutations of the heater.

Figure 2:
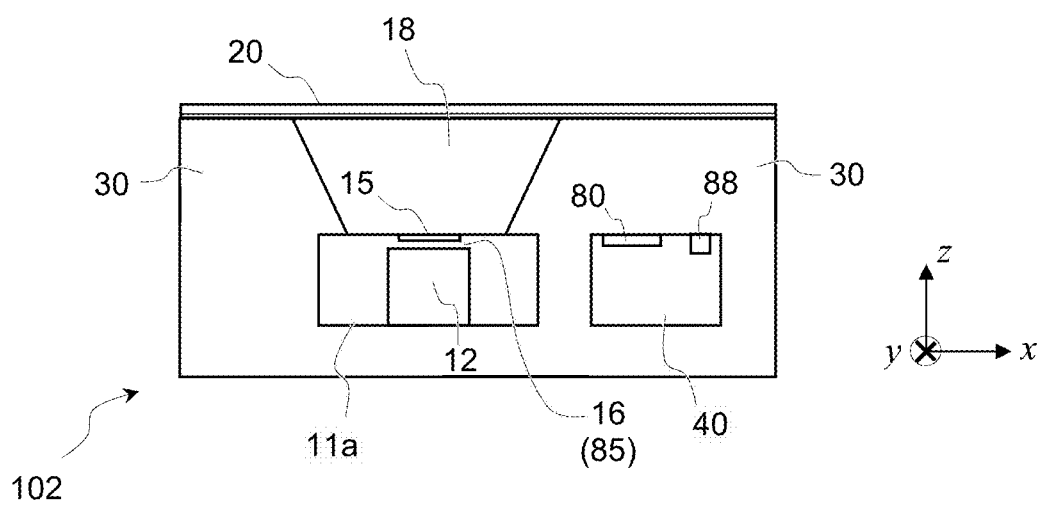
Figure 3:
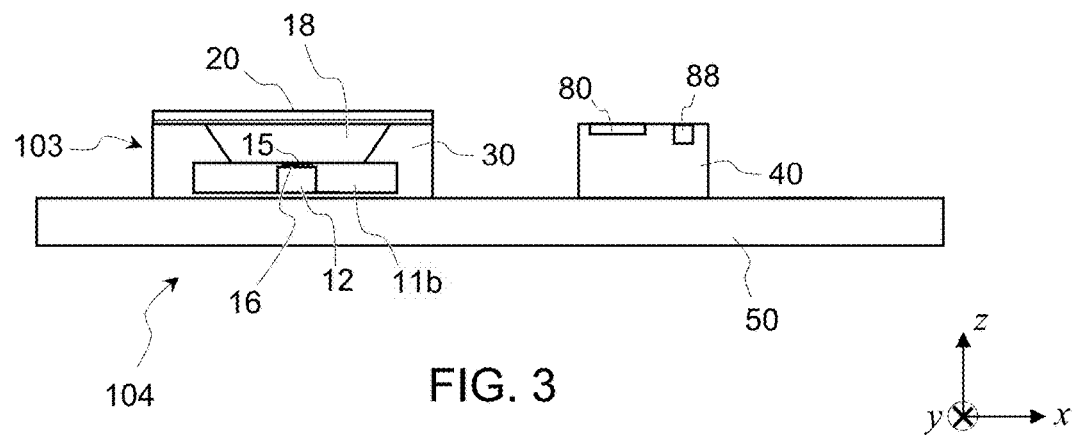
Figure 4:
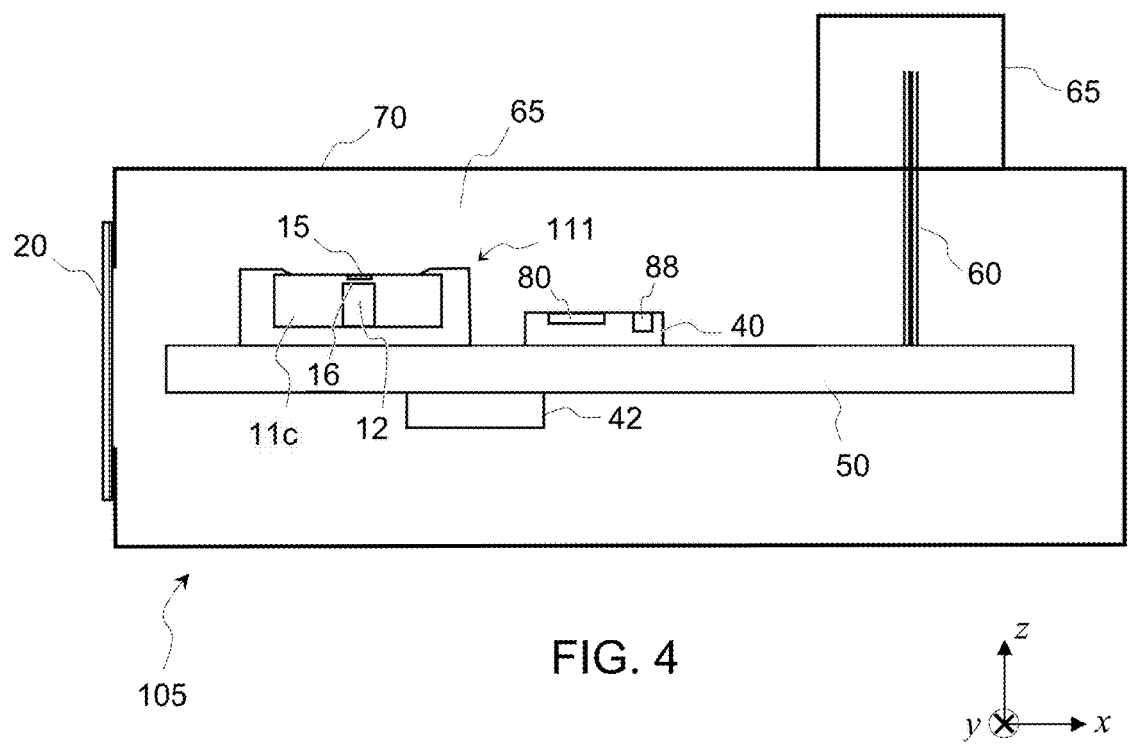

Preferred structural and mechanical designs of the gas sensors are now discussed in detail, in reference to FIGS. 1-8 and 13. Briefly, in such embodiments, the support structure may comprise an encapsulation 30, in which one or more chips are partly or fully embedded (as in FIGS. 1-3, 5, and 7), or a cap 32 on top of a chip (as in FIG. 6). The encapsulation 30 or the cap 32 may, together with a chip, define the cavity 18 that is otherwise closed by the filter 20, as in FIGS. 1-3, and 5-7. In variants, the support structure comprises a PCB 50, onto which one or more chips (e.g., semiconductor chips) are arranged, as in FIGS. 3 and 4. Moreover, the PCB may possibly be arranged in a container 70, which defines the cavity closed by the filter 20, as seen in FIG. 4. In all cases, at least some of the parts of the support structure may define (or contribute to define) the cavity 18, which is closed by the filter 20. Various hotplate configurations are possible too, including membrane-like configurations (as FIGS. 1-4, 8) and bridge configurations (as in FIG. 13). In variants, the hotplate may be configured as a slotted membrane, as known per se.

The gas sensor 101-110 preferably comprises one or more semiconductor chips, wherein such chips support one or more sensing elements 15 and comprise ICs of a circuitry 80 as previously discussed in reference to FIG. 9. As the one skilled in the art may appreciate, various architectures can be contemplated for the components 81-89 of the circuitry 80. Such components can notably be distributed across the various chips involved or, on the contrary, be essentially located on or in one chip (or more generally a substrate), as assumed in the examples of FIGS. 1-4.

The example of FIG. 1 involves a single semiconductor chip 11, defining a hotplate 16 (with an embedded heater 85) as a membrane supporting a single sensing element 15. All needed ICs 80 are integrated in the chip 11, off-centred from the sensing element 15. Electronic components of said ICs are here integrated in the body 11 of the chip, sufficiently far from the heater and hotplate, so as not to be thermally impacted by them. The chip further includes conductive tracks and/or electrical connectors (not shown) to connect the circuitry 80 to the heater 85 and the temperature sensor element 88. The temperature sensor element 88 is also integrated in the body of the chip 11 in this example, off-centred from the sensing element 15. The sensor 88 is placed far enough from the hotplate 16, so as to essentially sense a temperature of the filter 20 via the encapsulation material 30, which is assumed to be a sufficiently good thermal conductor in this example. The encapsulation material may for example comprise a moulding compound or a plastic.

The temperature sensor element 88 is preferably a built-in CMOS temperature sensor element. The whole semiconductor chip 11 can advantageously be built as a CMOS integrated platform. The latter may nevertheless include MEMS elements (microelectromechanical systems, e.g., forming the membrane 16) and ASIC circuits (e.g., aggregating components 81-84, 86, and 89 of the circuitry 80). For completeness, the gas sensor 101 further includes a leadframe 13, to carry signals from/to the chip. A die pad may possibly be provided and, e.g., manufactured from the same leadframe.

The examples of FIGS. 2 and 3 involve two semiconductor chips, i.e., a first semiconductor chip 11a, 11b (that includes the sensing element 15, the hotplate 16, and the heater 85), and a second semiconductor chip 40, in which the temperature sensor element 88 is integrated. The filter spans the cavity 18 formed above the first chip 11a, 11b in each case. ICs of the circuitry 80 are assumed to be integrated in the second chip 40 in this example. The chip 40 is nevertheless connected to the chip 11a, 11b, so as to receive signals from the sensing element 15 and supply power to the heater 85. That is, the second chip 40 regulates the temperature of the heater 85 (e.g., a resistively heated hotplate) of the first chip 11a, 11b, based on the estimated temperature of the filter 20. In variants, both chips may include ICs, where ICs in one chip connect to ICs in the other chip, so as to communicate signals from one chip to the other, as needed to operate the gas sensor 102, 104. Again, conductive tracks and/or any suitable electrical connectors (not shown) may be used.

For example, the first chip 11a may be a MEMS sensor chip or include MEMS components, while the second chip 40 may be an ASIC chip, where both the ASIC and MEMS chips form part of the same package 102, as illustrated in FIG. 2. In this example, the cavity 18 is defined in the first chip 11a, which supports the hotplate 16 (with an integrated heater 85). The first chip 11a and the second chip 40 are embedded in a same encapsulation 30 (the second chip 40 is fully embedded in that case, contrary to the first chip 11a). Again, the encapsulation 30 is assumed to be a satisfactory thermal conductor. Both chips communicate via external conductors (not shown), e.g., printed on the bottom side and/or lateral sides of the chips 11a, 40.

In variants, the first chip 11 and the second chip 40 may be arranged and connected via a same PCB 50, as in the example of FIG. 3.

The PCB may possibly be arranged in a container 70, to form a module 105, as in FIG. 4. That is, in the embodiment of FIG. 4, the support structure further comprises a container 70, in which an aperture is defined. The filter 20 now spans the aperture of the container 70, rather than an aperture defined by a chip package, as in FIGS. 1-3. The semiconductor chips 40, 42 and the chip package 111 (including chip 11c) are arranged on and connected to the PCB 50. The chip 11c includes the sensing element 15 and the hotplate 16 (with a heater). The second chip 40 comprises the temperature sensor element 88. ICs of the circuitry 80 are again assumed to be integrated in the second chip 40 in this example. The third chip 42 may for example include a humidity sensor, as discussed below in detail. The components 40, 42, 111 may be connected to each other or in pairs. The PCB is affixed to the container 70. A connector 65 of the module 105 is wired to the PCB via an electrical conductor 60, to connect the module 105 to other hardware components. In variants to the design proposed in FIG. 4, the ICs can be distributed across the components 40, 42, 111, so as for the gas sensing element 15 to be jointly operated by two or three of said components 40, 42, 111.

As evoked above, the gas sensor 105 may possibly include a humidity sensor, as illustrated in FIG. 4 (see also FIG. 11). The humidity sensor may for example be embodied as a separate chip 42, plugged onto the board 50, as assumed in FIG. 4. This humidity sensor may accordingly be connected to the circuitry 80 (itself integrated in the chip 40) via the PCB 50. Thus, the circuitry 80 can be configured to estimate an absolute humidity in the cavity 18 based on signals received from the humidity sensor 42. Note, the humidity sensor 42 may provide signals representative of the absolute humidity. In variants, the absolute humidity need be inferred (e.g., by the signal processor 82 of the circuitry 80) from signals provided by the humidity sensor 42. The circuitry may hence regulate the heater 85 by further taking into account the estimated absolute humidity, in addition to the measured (or estimated) temperature $T_f$ of the filter 20 and, if necessary, the measured (or estimated) temperature of the sensing element 15. This can be useful inasmuch as humidity too may damage the sensing elements, in particular when MOX sensors are used. For example, $WO_3$ sublimates in high absolute humidity conditions, above 300 C. Thus, lowering the temperature or switching off the hotplate in high absolute humidity conditions prevents $WO_3$ from sublimating. A humidity sensor 42 is thus preferably involved, in order to measure (or estimate) the absolute humidity used and thereby prevent damaging the MOX material of the sensing element 15.

FIGS. 5-7 depict various possible designs of chip package 106-108, as involved in embodiments. The circuitry (not shown) and the temperature sensor element (not shown) may possibly be integrated in the chip 22 or in another chip connected thereto.

In the example of FIG. 5, the gas sensor comprises a semiconductor chip 22 with the sensing element 15 on top. The semiconductor chip 22 is partly covered by an encapsulation 30 in the form of a mould and a lead frame 26 serves for contacting the chip from/to the outside. The support structure for the sensing element hence includes the lead frame 26 and the encapsulation 30. The chip 22 (excluding the hotplate 16) can be regarded as forming part of the support structure too, like the adhesive 25. The cavity 18 is defined by the various elements 22, 25, 26, 30 of the support structure. The cavity 18 is closed by the filter 20, which is formed by a combination of a carrier 24 and a filter layer 23 in this example. The filter 20 extends over the entire top surface of the encapsulation 30, to which the filter 20 is attached by means of the adhesive 25.

FIG. 6 depicts a similar design 107, except that the semiconductor chip 22 is now partly covered by a silicon cap 32. The cavity 18 is formed by the top surface of the chip 22, one or more internal surfaces of the silicon cap 32, and the adhesive 25, all being part of the support structure. In this example, the sensing element 15 is partly integrated in the chip 22, so as for a top surface thereof to be level with a surrounding, top surface of the chip 22 (similarly as in FIGS. 1-4 but contrary to FIG. 5).

FIG. 7 illustrates a further embodiment of the gas sensor 108, which is similar to FIG. 5, except that the filter 20 (including the layer 23 and the carrier 24) is now flipped and attached to the top surface of the support structure by means of a structured element 35, with a rim sealing the composite layer 23, 24. Thus, the carrier 24 now faces the cavity 18 while the filter layer 23 faces the environment of the gas sensor.

Figure 8:
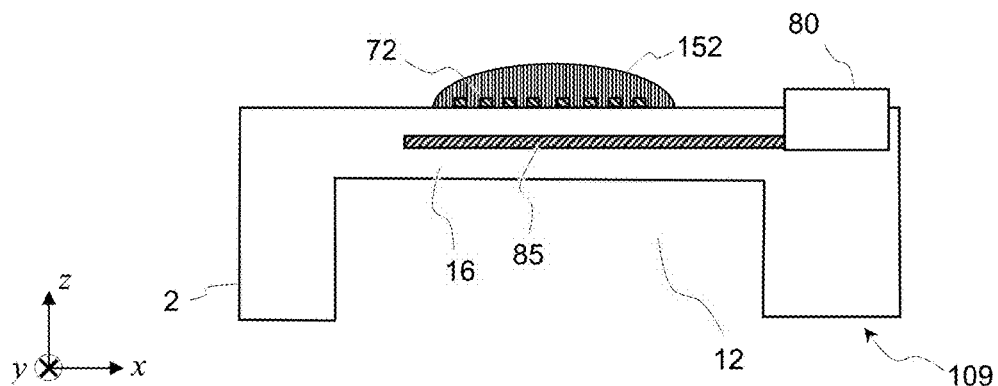

FIG. 8 illustrates a sub-assembly 109 of a gas sensor, which may be used in a gas sensor according to embodiments of the present invention. The depicted structure 109 is to be finalized by notably attaching a filter (not shown), e.g., to an encapsulation or a silicon cap, or a container. The structure shown comprises a sensing element 15 arranged on a semiconductor chip 22 that is etched on its backside, thereby defining a recess 12, as in FIGS. 1-7. The sensing element 15 covers electrodes (not shown) for supplying an electrical signal to an evaluation and control unit of the circuitry 80. The circuitry 80 is integrated in the semiconductor chip 22. It notably controls the heater 85, here integrated in the semiconductor substrate 22, at the level of the membrane 16.

Further variants to FIGS. 1-8 can be contemplated. E.g., the sensing element 15 can be arranged on/in a suspended membrane portion of a semiconductor substrate. Again, attention is drawn to WO2018053656 (A1).

In embodiments such as illustrated in FIGS. 1 to 8, an opening 12 (or a recess) is provided below the hotplate 16, 16a. More generally, the present devices will preferably include such an opening or recess 12. The latter is preferably distinct from the cavity 18, as in the examples of FIGS. 1-8. That is, the opening 12 and the cavity 18 pertain to distinct cavities in that case. The gas sensing element may for example be arranged on the hotplate 16, configured as a membrane, below which the opening 12 is provided. The opening 12 is typically defined in a substrate (which forms part of the support structure), so as to be located under the membrane 16 that connects to lateral portions of the substrate. This is typically realized in such a way that the lateral portions of the substrate do not appreciably heat when the membrane is heated, as noted earlier. By contrast to FIGS. 1-8, embodiments can be contemplated where this membrane is configured as a bridge or a slotted membrane. In such cases, the opening and the cavity may communicate or overlap (at least partly), as in FIG. 13.

Figure 13:
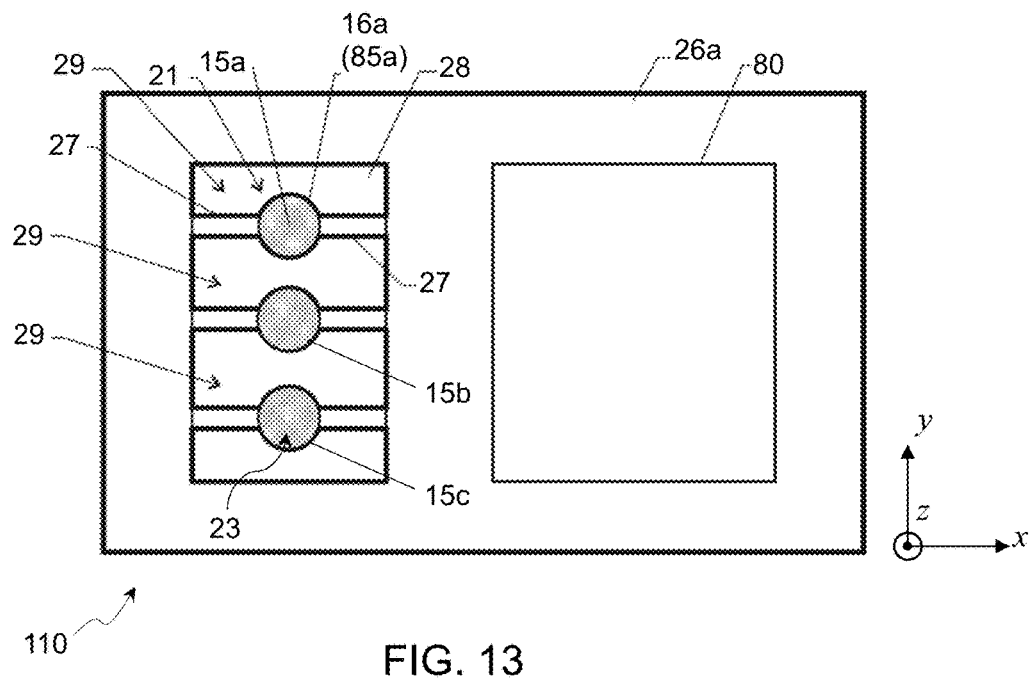
FIG. 13 is a top view of a further gas sensor, which comprises multiple patches of sensing materials in a bridge configuration, according to variants to the embodiments of FIGS. 1-8.

FIG. 13 is directed to a gas sensor 110 having a bridge configuration, as in embodiments. In this example, the sensor is a "multipixel" gas sensor 110. I.e., the sensor comprises a set of several patches (or "pixels") 15a-15c of sensing materials, wherein each of the patches may for example comprise a MOX material. Neither the filter nor the temperature sensor element is visible in the figure.

A opening (or recess) 28 (here seen from the top) is provided in the substrate 26a. Bridges 29 span this opening 28. Furthermore, the substrate carries a circuitry 80 similar to that of FIG. 9, for driving heaters and processing signals from the sensing elements 15a-15c and the temperature sensor element.

Each bridge 29 comprises a central region 85a forming a hotplate. Two arms 27 extend between each central region 85a and the substrate, thereby suspending the corresponding hotplate 85a over the opening 28. There are two arms 27 for each bridge 29 in the example of FIG. 13, the arms extending parallel to each other. Thus, the regions 85a may not be fully stabilized in the device and therefore can tend to tilt about the longitudinal axis of the arms 27. Thus, in variants to the design shown in FIG. 13, each central region 85a may be suspended by more than two arms, to prevent a tilting thereof, at the expense of increased thermal conduction between the central regions and the substrate.

The patches 15a-15c of sensing materials are arranged on substructures 27, 29 of the support structure 26a. In variants, the patches 15a-15c may be arranged on a same upper surface of the support structure 26a. The MOX material of each of the patches 15a-15c is in electrical communication with a subset of electrodes (not visible). The electrodes may for instance be electrically exposed to the patches thanks to suitably placed windows in a topmost dielectric layer (below the patches). Furthermore, one or more heaters (not visible either) are in thermal communication with the patches. The heaters may for example be formed out of a metal layer underneath the electrodes. The patches may possibly differ in terms of electrode designs and/or MOXs, to concomitantly sense several types of gas molecules.

In each of the embodiments of FIGS. 1-9 and 13, the heater(s) 85 may be a resistive heating element. For example, one may use a heater of tungsten, i.e., a heater comprising at least 50%, preferably at least 90%, of tungsten, to best withstand high temperatures. Several heaters may be provided, if necessary, to heat a plate (formed as a membrane, a slotted membrane, or a bridge), on which a patch of sensing material 152 is arranged. In variants, however, the hotplate is resistively-heated, such that no additional resistive element need be provided. The circuitry 80 is used to regulate the heater 85 (based on the filter temperature) and perform resistive measurements, i.e., to measure an electrical conductivity and/or resistivity of the patch(es) of sensing material.

Heating the sensing element(s) 15 will at most mildly increase the temperature of the filter in practice. As said, most critical heating effects to the filter may come from external sources, e.g., sunlight or other radiation sources such as other devices or components of the sensor, e.g., in a module 105 such as depicted in FIG. 4. Such a problem is particularly relevant in automotive applications, where sensors are embedded in vehicles, e.g., on or in thermal communication with the hood, the body, or the windshield of a car. Such parts may, when the vehicle is exposed to sunlight, achieve temperatures larger than 65 C, but cool down as soon as the car is moving, hence the benefits of the present regulation scheme.

Referring to FIGS. 11 and 10, another aspect of the invention is now described, which concerns a method of sensing a target gas (or target gases) with a gas sensor 101-110 as described earlier in reference to FIGS. 1-9, and 13. This method and its variants are collectively referred to as the "present methods" in the following. Such methods have been implicitly described in reference to the present gas sensors and are therefore only briefly discussed below.

Such methods rely on a gas sensor 101-110. As explained earlier, the gas sensor comprises a support structure that supports a hotplate 16 and defines a cavity 18. A gas filter 20 spans the cavity 18. The sensor further includes a circuitry 80 connecting a set of components, which include a temperature sensor element 88, a gas sensing element 15, and a heater 85 (in thermal communication with the sensing element 15).

Next, a series of steps are concurrently performed via (or by) the circuitry 80, which aim at operating the sensing element 15, estimating S40, S70 the temperature $T_f$ of the filter 20, and regulating S15 the heater 85 (step Sij refers to the flowchart of FIG. 11). Such steps are performed via the circuitry 80 if an external unit is involved, which utilizes the circuitry 80 to perform such steps, or by the circuitry 80 itself if the latter operates autonomously. In all cases, the circuitry 80 is involved to perform steps of the present methods.

The sensing element 15 is operated by energizing (i.e., supplying power to) S20 the heater 85, so as for the latter to heat the sensing element 15, and by processing S30 signals received from the sensing element 15. The temperature $T_f$ of the filter 20 is measured (or estimated) S40, S70 based on signals received from the temperature sensor element 88. This way, the extent to which the heater 85 is energized S20 is regulated S15; S20, S50, S60, S80 based on the estimated temperature of the filter 20.

In practice, the electrical power $P_h$ dissipated in the heater 85 is typically lowered (or the heater is switched off) S60 if the estimated temperature exceeds a (first) threshold temperature S50. The power dissipated in the heater may later be raised, or the heater be switched on S20, if the estimated temperature falls short of a (second) threshold temperature S80, as previously discussed.

FIG. 11 illustrates steps taken in a context were a heater 85 is assumed to be intermittently energized (i.e., switched off and on), for simplicity. In detail, once a sensor is exposed to an environment, step S10, its heater 85 can be switched on S20, to start sensing S30 target gas molecules from this environment and processing signals accordingly obtained from the gas sensing element. Concurrently to the sensing step S30, a temperature monitoring process is started, whereby the filter temperature is repeatedly (or continuously) estimated, step S40. If the monitored temperature happens to exceed a first threshold, step S50, then the heater is switched off S60. The signal processing S30 may possibly be paused, though not explicitly indicated in FIG. 11. The temperature monitoring process, however, continues S70 after switching off S60 the heater, as indicated by the dashed line to S70. Later on, if the monitored temperature is found to fall short of a second threshold, step S80, then the heater is switched on S20 again.

In multipixel embodiments such as previously described in reference to FIG. 13, the gas sensor 111 provided S10 comprises several sensing elements 15, these including distinct sensing materials, sensitive to distinct target gases when heated to respective working temperatures. Several heaters are used to heat the sensing elements 15; such heaters are in thermal communication with respective sensing elements 15 (they do not appreciably heat the filter 20). A temperature sensor element is used to measure the filter temperature. Several temperature sensor elements may be used to that aim, if necessary. In addition, several temperature sensor elements can be used to evaluate the temperatures of the gas sensing materials, if needed.

In scenarios involving multipixels as described above, it is advantageous to individually regulate S15 the heaters, in order to decouple the operation of the various sensing elements 15, as illustrated in the flowchart of FIG. 10.

Namely, the circuitry 80 can be used to operate the sensing elements 15 by energizing their respective heaters 85 (which accordingly heat respective sensing elements 15 at distinct working temperatures) and processing S30 signals received from the sensing elements 15. The working temperatures of the various sensing materials can possibly be monitored S90 according to temperature-controlled processes run in parallel for the various gas sensing elements 15. Concurrently, a temperature $T_f$ of the filter 20 is estimated S40, S70 based on signals received from one or more temperature sensor elements. Thus, the extents to which the heaters are energized can be individually regulated S15, in a decoupled fashion, by taking into account the measured (or estimated) temperature of the filter. Since the sensing materials have distinct characteristics, distinct threshold temperatures may need be considered for the various sensing elements.

For example, if the filter temperature exceeds a first threshold, then one or more of the heaters can be selected S15 to be switched-off. How to select such heaters further depends on their individual working temperatures, which may, or may not be, compatible with a current filter temperature. That is, at a given temperature of the filter, the latter may be substantially permeable to gas molecules that may damage only a subset of the sensing elements, owing to their distinct working temperatures. And similarly, heaters that were previously switched off may subsequently be switched on again, if the filter temperature permits, given the various thresholds associated to the various sensing elements.

While the present invention has been described with reference to a limited number of embodiments, variants and the accompanying drawings, it will be understood by those skilled in the art that various changes may be made, and equivalents may be substituted without departing from the scope of the present invention. In particular, a feature (device-like or method-like) recited in a given embodiment, variant or shown in a drawing may be combined with or replace another feature in another embodiment, variant or drawing, to obtain a new combination of features (not explicitly recited herein) that nevertheless remains within the scope of the present invention Various combinations of the features described in respect of any of the above embodiments or variants may accordingly be contemplated, which remain within the scope of the appended claims. In addition, many minor modifications may be made to adapt a particular situation to the teachings of the present invention without departing from its scope. Therefore, it is intended that the present invention not be limited to the particular embodiments disclosed, but that the present invention will include all embodiments falling within the scope of the appended claims. In addition, many variants not explicitly touched above can be contemplated. For example, various other materials and package designs can possibly be contemplated, as described, e.g., in WO2018053656 (A1).

The invention claimed is:

1. A gas sensor comprising:
    a hotplate;
    a support structure defining a cavity and supporting the hotplate;
    a gas selective filter held by the support structure and spanning the cavity;
    a circuitry including one or more integrated circuits; and connected to the circuitry:
        a temperature sensor element arranged on or in a part of the support structure, the temperature sensor element configured to sense a temperature $T_f$ of the filter;
        a gas sensing element arranged on or in the hotplate, so as to be sensitive to a target gas in the cavity; and
        a heater arranged on or in the hotplate, so as to be in thermal communication with the gas sensing element,
    wherein the circuitry is configured to:
        operate the gas sensing element by supplying power to the heater for the latter to heat the gas sensing element and processing signals received from the gas sensing element;
        estimate the temperature $T_f$ of the filter based on signals received from the temperature sensor element; and
        regulate an extent to which power is supplied to the heater based on the estimated temperature $T_f$ of the filter.

2. The gas sensor according to claim 1, wherein
    the circuitry is further configured to lower the extent to which power is supplied to the heater or to switch it off if the estimated temperature $T_f$ of the filter exceeds a threshold temperature.

3. The gas sensor according to claim 2, wherein
    the circuitry is further configured to raise the extent to which power is supplied to the heater or to switch it on if the estimated temperature $T_f$ of the filter falls short of a threshold temperature.

4. The gas sensor according to claim 2, wherein
    the circuitry is further configured to operate the gas sensing element by intermittently supplying power to the heater, whereby the circuitry switches off the heater if the estimated temperature $T_f$ of the filter exceeds a threshold temperature or switch on the heater if the estimated temperature falls short of a threshold temperature.

5. The gas sensor according to claim 1, wherein
    said temperature sensor element is a first temperature sensor element and the gas sensor further includes a second temperature sensor element connected to the circuitry,
    the circuitry is further configured to:
        estimate a temperature $T_s$ of the gas sensing element based on signals received from the second temperature sensor element; and
        regulate the extent to which power is supplied to the heater based on the estimated temperature $T_s$ of the gas sensing element, in addition to the estimated temperature $T_f$ of the filter.

6. The gas sensor according to claim 5, wherein the gas sensing element
    further comprises a metal oxide material, whereby the circuitry is configured to operate the gas sensing element by supplying power to the heater for the latter to reach a temperature that is between 100° C. and 600° C.

7. The gas sensor according to claim 5, wherein
    the gas sensor further includes a humidity sensor element connected to the circuitry, and
    the circuitry is further configured to:
        estimate an absolute humidity from signals received from the humidity sensor element; and
        regulate the extent to which power is supplied to the heater based on each of:
            the estimated absolute humidity,
            the estimated temperature $T_f$ of the filter; and
            the estimated temperature $T_s$ of the gas sensing element.

8. The gas sensor according to claim 1, wherein the filter comprises a fluoropolymer.

9. The gas sensor according to claim 8, wherein
    the circuitry is configured to lower the extent to which power is supplied to the heater or to switch it off if the estimated temperature $T_f$ of the filter exceeds a threshold temperature that is between 47° C. and 130° C.

10. The gas sensor according to claim 1, wherein
    the support structure further comprises a semiconductor chip.

11. The gas sensor according to claim 10, wherein
    the support structure further includes an encapsulation defining one or more surfaces of the cavity, the semiconductor chip being partly embedded in the encapsulation.

12. The gas sensor according to claim 10, wherein
    the temperature sensor element and all of said one or more integrated circuits are integrated in said chip.

13. The gas sensor according to claim 12, wherein
    the temperature sensor element is arranged in a body of the chip.

14. The gas sensor according to claim 10, wherein
said semiconductor chip is a first semiconductor chip and the gas sensor further comprises a second semiconductor chip, the temperature sensor element being arranged on or in the second semiconductor chip,
the second semiconductor chip further includes at least one of the one or more integrated circuits.

15. The gas sensor according to claim 1, wherein
the support structure comprises:
a container with an aperture spanned by the filter;
a printed circuit board; and
a connector wired to the printed circuit board,
the gas sensor further comprises one or more semiconductor chips,
the one or more semiconductor chips comprise the gas sensing element, the temperature sensor element, and the integrated circuits, and
the one or more semiconductor chips are arranged on the printed circuit board.

16. The gas sensor according to claim 1, wherein
the support structure further includes a substrate, which is structured so as to form a membrane.

17. The gas sensor according to claim 1, wherein
the hotplate is configured as one of: a membrane, a slotted membrane, and a bridge.

18. The gas sensor according to claim 1, wherein the filter is designed to filter gas molecules according to their sizes.

19. A method of sensing a target gas with a gas sensor, wherein the method comprises
providing a gas sensor comprising:
a hotplate;
a support structure defining a cavity and supporting the hotplate;
a gas selective filter maintained by the support structure and spanning the cavity;
a circuitry including one or more integrated circuits; and
a set of components, each connected to the circuitry, where said components include:
a temperature sensor element arranged on or in a part of the support structure, the temperature sensor element configured to sense a temperature $T_f$ of the filter;
a gas sensing element arranged on or in the hotplate, so as to be sensitive to a target gas in the cavity; and
a heater arranged on or in the hotplate, so as to be in thermal communication with the gas sensing element, and
via the circuitry:
operating the gas sensing element by:
supplying power to the heater for the latter to heat the gas sensing element; and
processing signals received from the gas sensing element;
estimating a temperature $T_f$ of the filter based on signals received from the temperature sensor element; and
regulating an extent to which power is supplied to the heater based on the estimated temperature $T_f$ of the filter.

20. The method according to claim 19, wherein
the set of components of the gas sensor provided comprises
several hotplates, including said hotplate, each of the hotplates supported by the support structure,
several gas sensing elements arranged on or in a respective one of the hotplate, the gas sensing elements including said sensing element, wherein the sensing elements are sensitive to distinct target gases,
several heaters, the latter including said heater, wherein said heaters are arranged on or in a respective one of the hotplates, so as to be in thermal communication with respective ones of the gas sensing elements, and
one or more temperature sensor elements, including said temperature sensor element, wherein said sensor elements are arranged on or in a part of the support structure, and
the method comprises, via the circuitry:
operating the gas sensing elements by
supplying power to their respective heaters for the latter to heat the respective gas sensing elements at distinct working temperatures, and processing signals received from the gas sensing elements;
estimating a temperature $T_f$ of the filter based on signals received from the one or more temperature sensor elements; and
individually regulating extents to which power is supplied to the heaters based, on the one hand, on the estimated temperature $T_f$ of the filter, and, on the other hand, on distinct threshold temperatures associated to the sensing elements.

* * * * *